United States Patent
Inoue et al.

(10) Patent No.: US 7,460,761 B2
(45) Date of Patent: Dec. 2, 2008

(54) CONTENT PLAYBACK METHOD, CONTENT PLAYBACK APPARATUS, CONTENT RECORDING METHOD, AND CONTENT RECORDING MEDIUM

(75) Inventors: Makoto Inoue, Kanagawa (JP);
Yoichiro Sako, Tokyo (JP); Katsuya Shirai, Kanagawa (JP); Toshiro Terauchi, Tokyo (JP); Yasushi Miyajima, Kanagawa (JP); Kenichi Makino, Kanagawa (JP); Motoyuki Takai, Tokyo (JP); Akiko Inoue, Saitama (JP)

(73) Assignee: Sony Corporation, Tokyo (JP)

( * ) Notice: Subject to any disclaimer, the term of this patent is extended or adjusted under 35 U.S.C. 154(b) by 912 days.

(21) Appl. No.: 10/893,170

(22) Filed: Jul. 16, 2004

(65) Prior Publication Data

US 2005/0041951 A1   Feb. 24, 2005

(30) Foreign Application Priority Data

Jul. 31, 2003  (JP) ............................. 2003-283417

(51) Int. Cl.
*H04N 5/91* (2006.01)
*H04N 7/00* (2006.01)
(52) U.S. Cl. .......................................... 386/46; 386/94
(58) Field of Classification Search .................. 386/46, 386/94, 125, 124, 83, 1
See application file for complete search history.

(56) References Cited

U.S. PATENT DOCUMENTS 6,269,216 B1 *   7/2001   Abecassis ..................... 386/46
2003/0060728 A1   3/2003   Mandigo

FOREIGN PATENT DOCUMENTS

| JP | 07303239   | * 11/1995 |
| JP | 08-087870  | 4/1996    |
| JP | 2001-320677 | 11/2001   |
| JP | 2003-101949 | 4/2003    |
| WO | WO 97/06531 | 2/1997   |
| WO | WO 97/07511 | 2/1997   |

* cited by examiner

*Primary Examiner*—Robert Chevalier
(74) *Attorney, Agent, or Firm*—Wolf, Greenfield & Sacks, P.C.

(57) ABSTRACT

Conditions for starting the playback of the next cut in the middle of the cut of a drama are assumed to be such that, for the first cut, a viewer/listener blinks two times in the detection time zone, and for the second cut, the pupil diameter of the viewer/listener has become 8 mm or more in the detection time zone. The CPU of a playback apparatus determines whether or not the conditions are satisfied when the cut is played back, and when the conditions are satisfied, the playback of the next cut is started even in the middle of the cut. In the case of music, when the rhythm of the respiration of the viewer/listener or the motion of the body is not in tune with the rhythm of the music, the playback of the next music is started even in the middle of the music.

6 Claims, 6 Drawing Sheets

FIG. 3

CONTENT OF CONTROL DATA

CONTROL DATA OF CUT FILE A

| DETECTION TIME ZONE | AFTER 15 SECONDS ELAPSES |
|---|---|
| REACTION OR STATE OF DETECTION TARGET | BLINKING (NICTITATING) |
| CUT CHANGE CONDITIONS | TWO OR MORE TIMES |

CONTROL DATA OF CUT FILE B

| DETECTION TIME ZONE | AFTER 20 SECONDS ELAPSES |
|---|---|
| REACTION OR STATE OF DETECTION TARGET | PUPIL DIAMETER |
| CUT CHANGE CONDITIONS | 8 mm OR MORE |

CONTENT PLAYBACK METHOD, CONTENT PLAYBACK APPARATUS, CONTENT RECORDING METHOD, AND CONTENT RECORDING MEDIUM

BACKGROUND OF THE INVENTION

1. Field of the Invention

The present invention relates to a content playback method and apparatus for playing back video images, for example, of dramas, still images, for example, of photographs and illustrations, audio, for example, of dramas and music, and content, for example, of documents (text) such as novels; a content recording method for use with the content playback method; and a content recording medium for use with the content playback method.

2. Description of the Related Art

Content is that which can be recognized visually and auditorily by people, and is represented by signals. The playback of content presents the content to people (viewers/listeners).

In dramas formed of a video image and audio, which are presented on a television or a video unit, and also in dramas formed of only audio, which are presented on a radio, a timing of changing from one cut to the next cut is important.

If the cut change timing is too slow, a tedious and slow product with an unsuitable tempo is produced. Conversely, if the cut change timing is too fast, important matters are not seen, and when a touching scene is playing, it is not possible to fully appreciate the moment.

In general, units shorter than a scene are referred to as "cuts", but here, all divisions are called "cuts" regardless of the length of time.

In Japanese Unexamined Patent Application Publication No. 11-250629, a technology related to recording and playback of audio content is disclosed in which audio title playback units are structured as cells, and management information such as the playback time and the time required for a user to operate the playback apparatus are added to the audio content in which the playback sequence of content is defined by defining the playback sequence of the cells, thereby improving ease of operation during playback.

However, an appropriate cut change timing depends on the content of the whole drama and the content of each cut, and is also influenced by the personality of the viewer/listener and the degree of concentration at that time. Thus, it is difficult to produce a drama in such a manner that the cut is changed at a timing appropriate for any viewer/listener.

It is considered that the cut is changed at an appropriate timing by the operation of the viewer/listener. However, it is inconvenient for the viewer/listener to perform a changing operation for each cut, and operation is sometimes not possible because the hands are occupied by something else.

Furthermore, as described in Japanese Unexamined Patent Application Publication No. 11-250629, even if the playback time and the time required for operation are recorded in advance, this does not make it possible to change the cut at an appropriate timing corresponding to the respective times of the individual viewers/listeners.

SUMMARY OF THE INVENTION

Accordingly, an object of the present invention is to provide a content playback method for playing back content formed of a plurality of partial contents, in which a change from certain partial content to the next partial content can be made at an appropriate timing corresponding to the respective times of the individual viewers/listeners.

In this specification, elements which correspond to cuts in a drama, which are portions of content, and which constitute the whole content as a result of being played back in sequence, are referred to as "partial content". In content other than a drama, partial content corresponds to each photo of a photograph collection, one page of a book, one piece or one movement of music, etc.

In an aspect, the present invention provides a content playback method of sequentially playing back content formed of a plurality of partial contents, the content playback method comprising the steps of: detecting bio-information of a viewer/listener who is playing back partial content; and determining whether or not the detected bio-information satisfies predetermined conditions, and starting the playback of the next partial content when the conditions are satisfied.

In the above-described content playback method of the present invention, playback control means of a content playback apparatus determines whether or not the reaction or the state of a viewer/listener who is playing back partial content, the reaction or the state being detected by detection means such as a video camera or a biometric sensor, satisfies predetermined conditions, such as blinking occurring two or more times, the pupil diameter becoming 8 mm or more, and the state in which the body motion is not in tune with the rhythm of the music being played back continuing for a fixed time. When the conditions are satisfied, the playback of the next partial content is started.

Therefore, in the case of a drama, when the viewer/listener is surprised or is paying attention, a change is made to the next cut even in the middle of the current cut, and in the case of music, when the viewer/listener is not interested in the music or is not concentrating on the music, a change is made to the next music even in the middle of the current music. In this manner, a change is made from certain partial content to the next partial content at an appropriate timing corresponding to the respective times of the individual viewers/listeners without requiring the operation by the viewer/listener.

As described above, according to the present invention, a change can be made from certain partial content to the next partial content at an appropriate timing corresponding to the respective times of the individual viewers/listeners without requiring the operation by the viewer/listener.

BRIEF DESCRIPTION OF THE DRAWINGS

FIG. 3 shows an example of condition contents;

DESCRIPTION OF THE PREFERRED EMBODIMENTS

Embodiment when Video-Audio Content is Played Back: FIGS. 1 to 6

Figure 1:
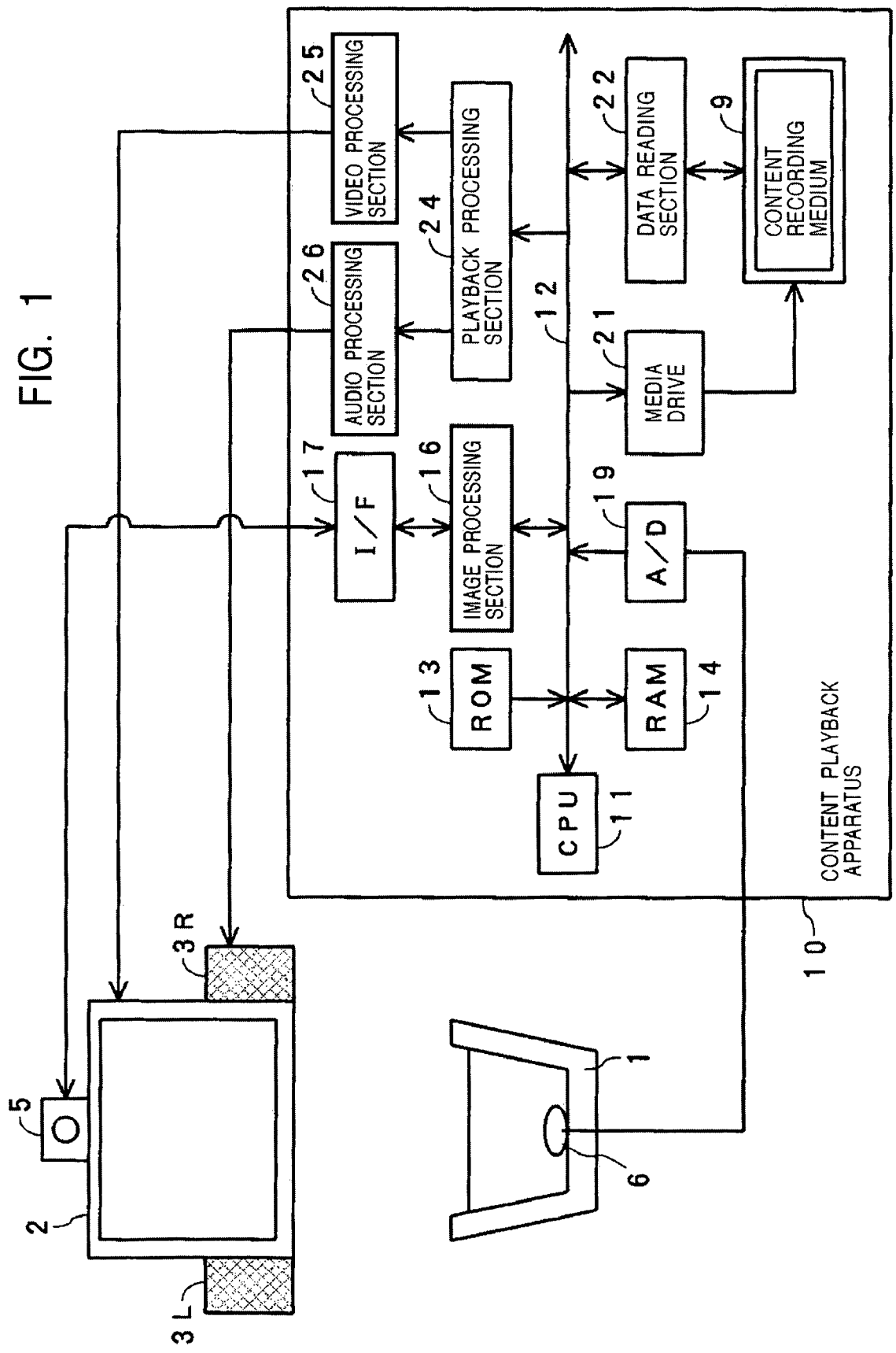
FIG. 1 shows an example of a content playback apparatus according to the present invention.

FIG. 1 shows an example of a content playback apparatus according to the present invention, and also shows a case in which video-audio content recorded on a content recording medium is to be played back.

A viewer/listener, while, for example, sitting on a chair 1, views a video image displayed on a display unit 2 and listens to audio output from the left and right speakers 3L and 3R, the video image and the audio being played back from a content recording medium 9 in a content playback apparatus 10.

Detection of the Reaction or State of the Viewer/Listener: FIG. 1

In this example, a video camera 5 is provided on the display unit 2, and a biometric sensor 6 is provided on the chair 1.

Both the video camera 5 and the biometric sensor 6 detect the bio-information of the viewer/listener. The bio-information generally refers to physiological, biochemical, or physical reaction or state of a person, such as the heart beat, the pulse, the blood pressure, the respiration, the brain waves, the skin perspiration, the skin resistance, the myoelectric potential, the bodily surface temperature, blinking (nictitating), the pupil diameter, the produced vocal sound, the facial expression, the posture (face direction and bodily direction), and the body motion (motion of body).

In this example, in the video camera 5, the face of the viewer/listener who is playing back content is recorded, and as will be described later, the image data obtained from the video camera 5 is processed by the content playback apparatus 10, thereby detecting the blinking (nictitating) and the pupil diameter of the viewer/listener. The biometric sensor 6 is, for example, a body motion sensor or a respiration sensor, which detects the body motion or the respiration of the viewer/listener who is playing back partial content.

Configuration of the Content Playback Apparatus: FIG. 1

The content playback apparatus 10 of this example includes a CPU 11. Connected to the bus 12 of the CPU 11 are a ROM 13 in which programs executed by the CPU 11 and fixed data are written, a RAM 14 in which a program and data are expanded, an image processing section 16 for processing image data obtained from the video camera 5 in order to analyze the image recorded by the video camera 5, an interface 17 for connecting the image processing section 16 to the video camera 5, and an A/D converter 19 for converting the bio-information of an analog signal obtained from the biometric sensor 6 into digital data.

The content recording medium 9 loaded into the content playback apparatus 10 is driven by a media drive 21, and data composed of content data and control data (to be described later), which are recorded on the content recording medium 9, is read by a data reading section 22.

The control data within the read data is analyzed by the CPU 11 and is used for content playback control. The content data within the read data, that is, video-audio data, is separated into video data and audio data at a playback processing section 24.

For the separated video data, processing, such as expansion decoding and conversion into an analog signal, is performed thereon at a video processing section 25, and thereafter, the video data is output to the display unit 2, whereby a video image is displayed. For the separated audio data, processing, such as expansion decoding and conversion into an analog signal, is performed thereon at an audio processing section 26, and thereafter, the audio data is output to the speakers 3L and 3R, from which audio is output.

Operations, such as the starting and stoppage of the video camera 5, are performed by the CPU 11 of the content playback apparatus 10 via the image processing section 16 and the interface 17, for example, by the operation of the viewer/listener at the content playback apparatus 10.

Figure 2:
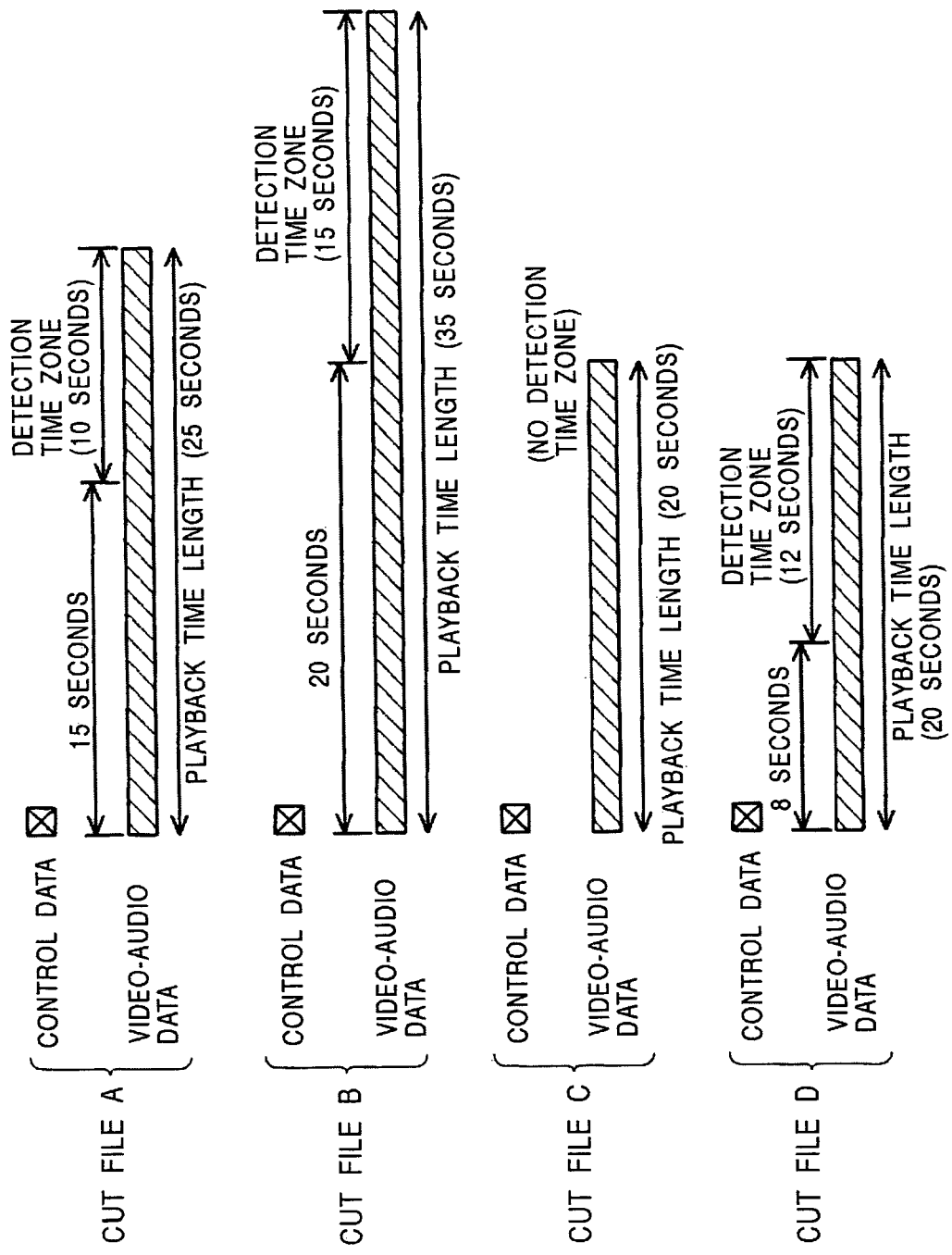
FIG. 2 shows an example of control data.

Content Recording Medium and Content Recording Method: FIGS. 1 to 3

In this example, on the content recording medium 9, video-audio data of a drama is recorded as content. The drama is produced so that a plurality of cuts (divisions) are played back in a predetermined sequence. Furthermore, in the video-audio data of this drama, control data is added for each cut.

FIG. 2 shows the situation. The cut files A, B, C, and D are such that video-audio data and control data of each cut are combined.

The playback time length of the video-audio data of the cut differs from cut to cut. In this example, in the cut file A, the playback time length is 25 seconds; in the cut file B, it is 35 seconds; in the cut file C, it is 20 seconds; and in the cut file D, it is 20 seconds. The playback time length is a time length when the cut in question is played back from the beginning up to the end.

The control data of each cut file is such that conditions, which are related to the reaction or state of the viewer/listener who is playing back the current cut, for starting the playback of the next cut in the middle of the current cut are described. More specifically, in this example, the conditions (the conditions in a broad sense) are the time zone in which the reaction or state of the viewer/listener who is playing back the content is detected, the reaction or state to be detected in this detection time zone, and the cut change conditions (the conditions in a narrow sense) regarding the reaction or state. The detection time zone is set at the end portion of the cut for the reasons to be described later.

In the example of FIG. 2, for the cut file A of the first cut, the detection time zone is set as "after 15 seconds elapses", that is, is set as the 10 seconds from the time after 15 seconds elapses from when the current cut is started up to the completion time of the current cut. As shown in FIG. 3, the reaction or state of the detection target is set as "blinking", and the cut change conditions are set as "two or more times".

This means that, regarding the first cut, during the playback thereof, if the blinking of the viewer/listener is detected two times in the detection time zone of the 10 seconds of the end portion, the playback of the next second cut should be started at the time the detection is made even in the middle of the current cut. The time at which the viewer/listener continuously blinks two or more times is when the viewer/listener is surprised at the current cut.

For the cut file B of the second cut, the detection time zone is set as "after 20 seconds elapses", that is, is set as the 15 seconds from the time after 20 seconds elapses from when the current cut is started up to the completion time of the current cut. As shown in FIG. 3, the reaction or state of the detection target is set as the "pupil diameter", and the cut change conditions are set as "8 mm or more".

This means that, regarding the second cut, during the playback thereof, if it is detected that the pupil diameter of the viewer/listener has become 8 mm or more in the detection time zone of the 15 seconds of the end portion, the playback of the next third cut should be started at the time the detection is made even in the middle of the current cut. The time at which the pupil diameter of the viewer/listener becomes 8 mm or more is when the viewer/listener is paying attention to the current cut.

The example of FIG. 2 shows that, for the cut file C of the third cut, the detection time zone is not shown, and the reaction or state of the detection target and the cut change conditions are also not shown. This means that, regarding the third cut, after the current cut is played back up to the end, the playback of the next fourth cut should be started regardless of the reaction or state of the viewer/listener.

For the cut file D of the fourth cut, the detection time zone is set as "after 8 seconds elapses", that is, it is set as the 12 seconds from the time after 8 seconds elapses from when the current cut is started up to the completion time of the current cut. Although omitted in FIG. 3, if the reaction or state of a particular detection target satisfies particular conditions, the playback of the next fifth cut should be started at that time.

Although omitted in FIG. 2, also, for the fifth and subsequent cuts, control data is added to the video-audio data. For the final cut, the detection time zone is not shown, and it is assumed that the current cut is played back up to the end.

The drama producer produces a drama, and when recording the drama as content on the content recording medium 9, the drama producer determines whether or not the cut change for each cut in the middle of the current playback should be permitted according to the content of the current cut, the content of the next cut, and further the content of the whole drama. Furthermore, regarding the cut for which a cut change in the middle of the playback is permitted, as described above, the detection time zone, the reaction or state of the detection target, and the cut change conditions for the reaction or state are determined.

In addition to the above-described "surprise" regarding the first cut and the above-described "attention" regarding the second cut, setting is possible, for example, in a sad cut, when the sobbing of the viewer/listener is detected, the scene proceeds to the next cut, and in a hair-raising cut of a horror drama, when it is detected that the viewer/listener shakes with terror, the scene proceeds to the next cut.

The reason why the detection time zone is set at the end portion of the cut in the manner described above is as follows. In any time zone of the cut, when a certain reaction or state is detected under fixed conditions, if the playback of the current cut is stopped and the playback of the next cut is started, even when the viewer/listener shows a fixed reaction not because the viewer/listener reacts to the drama but for some other reasons, the playback of the current cut is stopped, and the viewer/listener might miss seeing the essential portion of the first half of the cut.

In contrast, when the detection time zone is set at the end portion of the cut, the viewer/listener does not miss seeing the first half of the cut. For this reason, video and audio corresponding to the lingering moment of the first half such as that which does not adversely affect the understanding of the content of the drama even if it is not necessarily viewed should be recorded at the end portion where the detection time zone of the cut for which the cut change in the middle of the playback is permitted is set. The end portion where the detection time zone is set is a portion which acts as a kind of "allowance". From this viewpoint, the cut for which a cut change in the middle of the playback is permitted is produced a little longer than the length required to convey the content of the drama.

The control data is added to the header part of the video-audio data of the cut, or is recorded, together with the video-audio data of the cut, on the content recording medium 9 in such a manner as to be time-divided in the beginning portion of the video-audio data of the cut. Alternatively, if it can be known about which cut the control data in question corresponds to the video-audio data of, the control data may be recorded in a recording area differing from the recording area of the video-audio data of the content recording medium 9.

Figure 4:
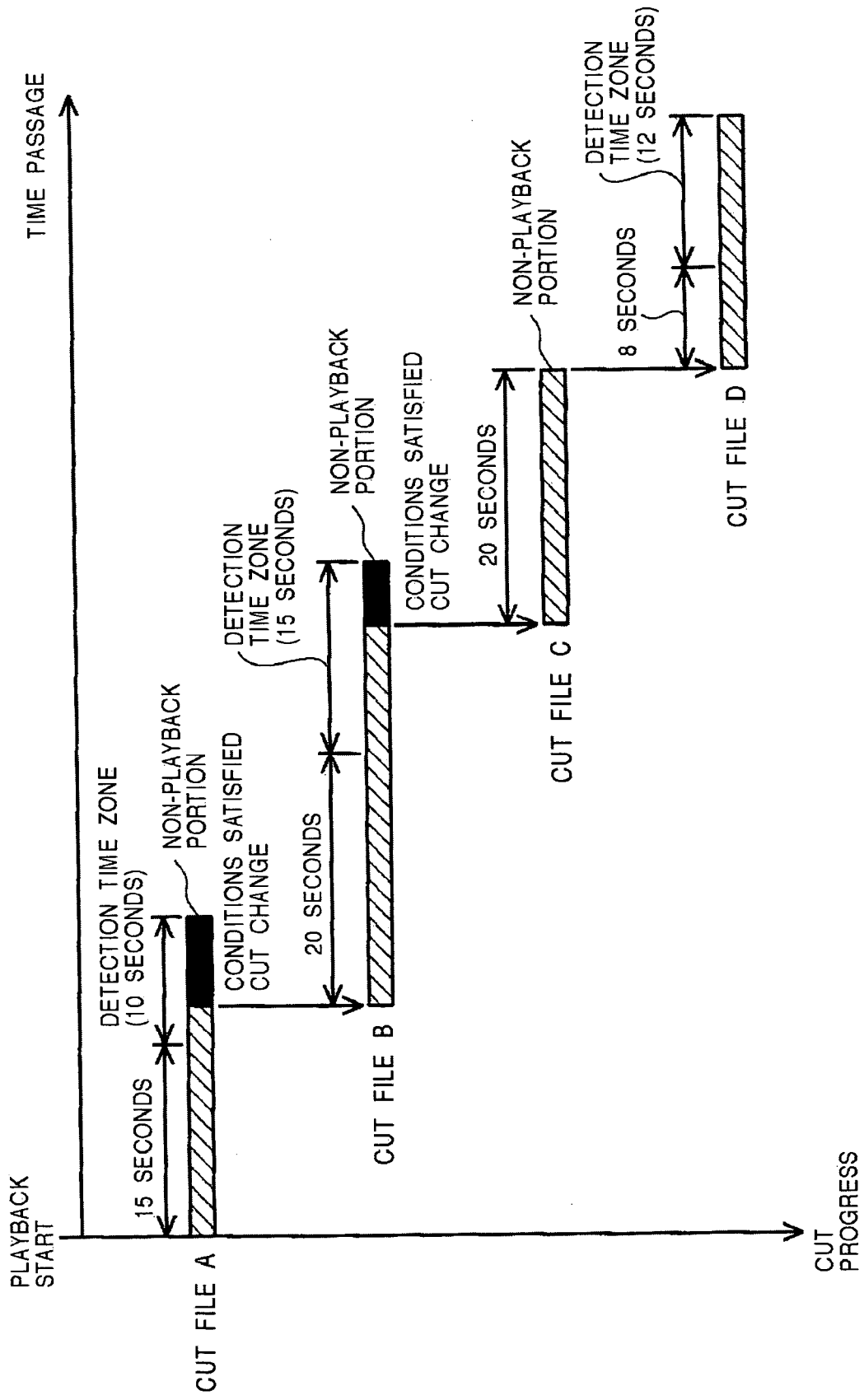
FIG. 4 shows an example of content playback control.
Figure 5:
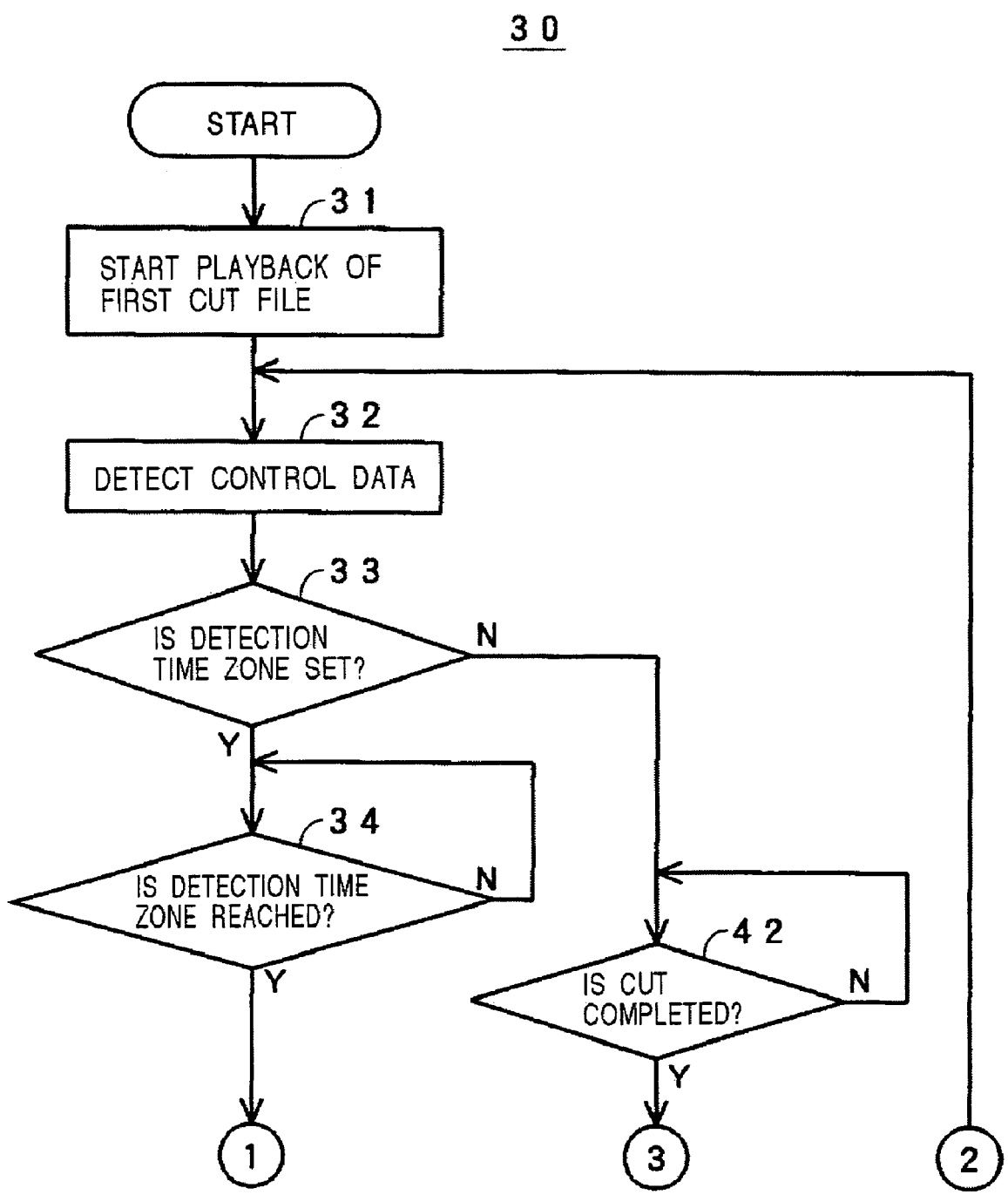
FIG. 5 shows portions of an example of a content playback control process performed by a CPU of the content playback apparatus.
Figure 6:
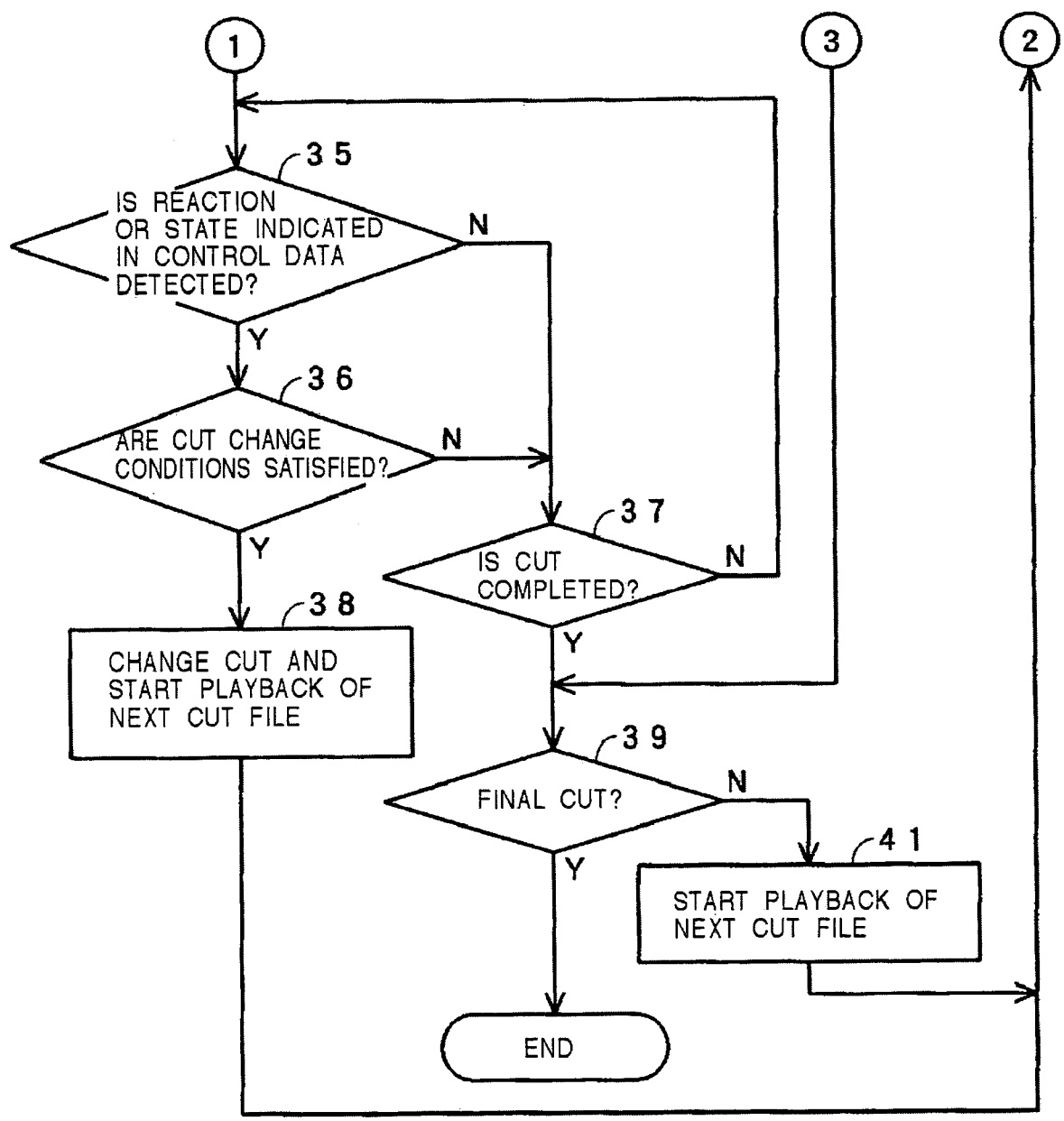
FIG. 6 shows the other portions of the example of the content playback control process performed by the CPU of the content playback apparatus.

Content Playback Control: FIGS. 4 to 6

When each cut of a drama is to be played back, the CPU 11 of the content playback apparatus 10 analyzes the control data so as to control the playback of the cut.

In the above-described example, for the first cut, since the control data of the cut file A is set to change the cut if "blinking" is detected two times in the specified detection time zone, in the 10 seconds from the time after 15 seconds elapses from when the first cut is started up to the completion time of the current cut, the output of the image processing section 16, that is, the analysis result of the image recorded by the video camera 5, is received to determine whether or not blinking is detected two times.

When blinking is detected two times, as shown in FIG. 4, at the time when the detection is made, the playback of the next second cut is started. In this case, as indicated by being filled-out in black in FIG. 4, the portion subsequent to the cut change time of the first cut is not played back.

Although not shown in FIG. 4, when the "blinking" is not detected two times in the detection time zone (only one blinking is detected or no blinking is detected), the current first cut is played back up to the end, after which the playback of the next second cut is started.

For the second cut, since the control data of the cut file B is set to change the cut if it is detected that the "pupil diameter" has become 8 mm or more in the specified detection time zone, in the 15 seconds from the time after 20 seconds elapses from when the second cut is started up to the completion time of the current cut, the output of the image processing section 16, that is, the analysis result of the image recorded by the video camera 5, is received to determine whether or not the fact that the "pupil diameter" has become 8 mm or more is detected.

Then, when it is detected that the "pupil diameter" has become 8 mm or more, as shown in FIG. 4, the playback of the next third cut is started when the detection is made. In this case, as indicated by being filled-out in black in FIG. 4, the portion subsequent to the cut change time of the second cut is not played back.

Although not shown in FIG. 4, when it is not detected that the "pupil diameter" has become 8 mm or more in the detection time zone, the current second cut is played back up to the end, after which the playback of the next third cut is started.

For the third cut, since the detection time zone is not set in the control data of the cut file C, the current third cut is played back up to the end, after which the playback of the next fourth cut is started.

Regarding the fourth and subsequent cuts, the CPU 11 controls the playback of the cuts according to the content of the control data.

FIGS. 5 and 6 show an example of the above-described content playback control process performed by the CPU 11.

In the content playback control process 30 of this example, initially, in step 31, the playback of the first cut file is started. In the next step 32, the control data of the cut file in question is detected. Then, the process proceeds to step 33, where it is determined whether or not a detection time zone is set in the control data.

When the detection time zone is set, the process proceeds from step 33 to step 34, where it is determined whether or not the detection time zone is reached. When the detection time zone is reached, the process proceeds to step 35, where it is determined whether or not the reaction or state of the detection target, which is indicated in the control data, is detected.

In the above-described example, the reaction or state is "blinking" for the first cut, and it is the "pupil diameter" for the second cut.

When it is determined in step 35 that the reaction or state of the detection target is detected, the process proceeds to step 36, where it is determined whether or not the cut change conditions are satisfied. When the cut change conditions are not satisfied, the process proceeds to step 37, where it is determined whether or not the current cut (in the detection time zone) is to be completed. When the current cut is not to be completed, the process returns to step 35, where it is determined whether or not the reaction or state of the detection target is detected.

When it is determined in step 35 that the reaction or state of the detection target is not detected, the process proceeds directly from step 35 to step 37, where it is determined whether or not the current cut (in the detection time zone) is to be completed. When the current cut is not to be completed, the process returns to step 35, where it is determined whether or not the reaction or state of the detection target is detected.

That is, in steps 35, 36, and 37, it is determined whether or not the reaction or state of the detection target is detected every fixed time period until the cut change conditions are satisfied or until the current cut (in the detection time zone) is completed.

In the above-described example, regarding the first cut, when the first "blinking" is detected, it is counted as one time in step S35. Thereafter, when the second "blinking" is detected, it is counted as a total of two times in step S35, and it is determined in step 36 that the cut change conditions are satisfied. Regarding the second cut, when it is determined in step 35 that the "pupil diameter" is detected, it is determined in step 36 whether or not the "pupil diameter is 8 mm or more". When the pupil diameter is 8 mm or more, it is determined that the cut change conditions are satisfied.

When it is determined in step 36 that the cut change conditions are satisfied, the process proceeds to step 38, where the cut is changed and the playback of the next cut file is started. The process then returns to step 32, where processing of step 32 and subsequent steps is repeated for the next cut.

On the other hand, when it is determined in step 37 that the current cut (in the detection time zone) is to be completed without detecting the reaction or state of the detection target or without satisfying the cut change conditions, the process proceeds to step 39, where it is determined whether or not the current cut is the final cut. If it is not the final cut, the process further proceeds to step 41, where the playback of the next cut file is started and thereafter, the process returns to step 32, where processing of step 32 and subsequent steps is repeated for the next cut.

When it is determined in step 33 that the detection time zone is not set in the control data, the process proceeds to step 42, where it is determined whether or not the current cut is to be completed. When it is determined that the current cut is to be completed, the process proceeds to step 39, where it is determined whether or not the current cut is the final cut. If it is not the final cut, the process further proceeds to step 41, where the playback of the next cut file is started and thereafter, the process returns to step 32, where processing of step 32 and subsequent steps is repeated for the next cut.

In the above-described example, for the third cut, processing of steps 33, 42, 39, and 41 is performed in sequence.

When it is determined in step 39 that the current cut is the final cut, the content playback control process is completed.

The above example shows a case in which, when the reaction or state that satisfies the cut change conditions, such as the "blinking being two or more times" or the "pupil diameter being 8 mm or more", is detected, the cut is changed immediately, and the playback of the next cut is started. Alternatively, the construction may be formed in such a way that the cut is changed after a fixed time, such as one second or several seconds from the time when the reaction or state that satisfies the cut change conditions is detected, and the playback of the next cut is started.

Another Example of Content Playback

The above example shows a case in which video-audio content recorded on a content recording medium is played back. The above content playback method can also be applied to a case in which video-audio content transmitted from a transmission source such as a distribution source server or a broadcasting station over a network or in the form of radio waves is received and played back.

In this case, the transmission source transmits the above-described control data together with video-audio content, for example, video-audio data of a drama.

The content playback apparatus on the viewer/listener side receives the control data and the video-audio content, and plays back the video-audio content. In this case, in order to start the playback of the next partial content in the middle of the partial content, for example, in order to start the playback of the next cut in the middle of the current cut, the content playback apparatus is configured in such a way that, at the above-described playback start time in a portion of the detection time zone, at least the beginning portion of the next partial content, for example, the beginning portion of the next cut, is prestored in the storage section of the content playback apparatus.

Embodiment when Audio Content is Played Back

The content playback method of the present invention can also be applied to a case in which only audio content is to be played back.

Audio content is, for example, music such that a plurality of pieces of music are played back in a predetermined sequence. The above-described control data is added for each piece of music to the music data, or conditions for starting the playback of the next music in the middle of the music are set commonly to each music.

More specifically, when the viewer/listener is interested in the music and is concentrating on the music, the rhythm of the respiration of the viewer/listener is in tune with the rhythm of the music and the motion of the body is also in tune with the rhythm of the music; or the viewer/listener sits still. In contrast, when the viewer/listener is not interested in the music, is not concentrating on the music, or is bored, the rhythm of the respiration of the viewer/listener is not in tune with the rhythm of the music, and the motion of the body is also not in tune with the beat of the music.

Therefore, the conditions for starting the playback of the next music in the middle of the music are assumed to be such that, for example, the fact that the rhythm of the respiration of the viewer/listener or the motion of the body is not in tune with the rhythm of the music over a particular time is detected.

Such reaction or state of the viewer/listener can be detected by the respiration sensor and the body motion sensor shown as the biometric sensor 6 in FIG. 1.

Furthermore, when the conditions for starting the playback of the next music in the middle of the music are set commonly for each music in this manner, the conditions can be set in advance within the content playback apparatus.

The content playback apparatus is configured in such a way that, when the CPU of the content playback apparatus determines that the conditions are satisfied, the playback of the next music is started.

Regarding such music content, also, as in the case of electronic music distribution, when content is transmitted from the transmission source, and the content is received and played back by the content playback apparatus on the viewer/listener side, the content playback method of the present invention can be applied.

In this case, the above-described control data may be transmitted from the transmission source. Also, when the conditions for starting the playback of the next music in the middle of the music are set commonly for each music in the manner described above, the conditions can be set in advance within the content playback apparatus.

However, in order to start the playback of the next music in the middle of the music, the content playback apparatus is configured in such a way that, at the time when the playback in a portion of the detection time zone is started, at least the beginning portion of the next music is prestored in the storage section of the content playback apparatus.

Embodiment when another Type of Content is Played Back

The content playback method of the present invention can also be applied to a case in which an electronic document, such as a so-called electronic novel, formed of text data, diagrams, photographs, etc., which is transmitted from the transmission source or which is recorded on a recording medium, is played back in a PDA (Personal Digital Assistant) or a cellular phone terminal.

In this case, an electronic document such as an electronic novel is played back and displayed for each page. Conventionally, by the operator performing an operation of turning a page at the operation section, the next page is played back and displayed.

In contrast, in this example, conditions for stopping the playback and display of a particular page and for playing back and displaying the next page are set in the content playback apparatus of the present invention, such as a PDA or a cellular phone terminal.

More specifically, when the viewer/listener (reader) is concentrating on the page and gazes at the page, the viewer/listener sees the display from the front, but when the viewer/listener is not concentrating on the page, the viewer/listener turns away his/her eyes from the display.

Therefore, the conditions for stopping the playback and display of a particular page and for playing back and displaying the next page in this case are assumed to be such that, for example, the fact that the state in which the face direction of the viewer/listener is averted from the display continues over a particular time is detected.

Such reaction or state of the viewer/listener can be detected by a camera provided in a content playback apparatus such as a PDA or a cellular phone terminal. For such a camera, the camera of a cellular phone terminal with a camera can also be used.

The content playback apparatus is configured in such a way that, when the CPU of the content playback apparatus determines that the conditions are satisfied, the next page is played back and displayed.

The conditions for stopping the playback and display of a particular page and for playing back and displaying the next page may also be assumed to be such that the fact that the viewer/listener takes a big breadth or utters sound is detected. Such reaction or state of the viewer/listener can be detected by a respiration sensor or a microphone provided in the content playback apparatus.

According to the above, when the viewer/listener wants to turn a page, the viewer/listener can turn a page by taking a big breadth or uttering sound without the intervention of manual operation at the content playback apparatus.

What is claimed is:

1. A content playback method of sequentially playing back content formed of a plurality of segments of partial content, said content playback method comprising the steps of:
   detecting bio-information of a viewer/listener who is playing back a segment of partial content; and
   determining whether or not detected bio-information satisfies predetermined conditions, and starting playback of a next segment of partial content when the predetermined conditions are satisfied, wherein the bio-information of the viewer/listener who is playing back partial content is detected in a detection time zone determined for each segment of partial content.

2. The content playback method according to claim 1, wherein said detection time zone is set as a time zone at the end portion of the segment of partial content.

3. The content playback method according to claim 1, wherein said predetermined conditions are determined for each segment of partial content.

4. A content playback apparatus for sequentially playing back content formed of a plurality of segments of partial, said content playback apparatus comprising:
   detection means for detecting bio-information of a viewer/listener who is playing back a segment of partial content; and
   playback control means for determining whether or not detected bio-information satisfies predetermined conditions, and for starting playback of a next segment of partial content when the predetermined conditions are satisfied, wherein said playback control means determines whether or not the bio-information detected by said detection means in a detection time zone determined for each segment of partial content satisfies predetermined conditions.

5. The content playback apparatus according to claim 4, wherein said detection time zone is set as a time zone at the end portion of the segment of partial content.

6. The content playback apparatus according to claim 4, wherein said predetermined conditions are determined for each segment of partial content.

* * * * *